United States Patent [19]

Short

[11] 4,366,901

[45] Jan. 4, 1983

[54] IN SITU REHYDRATING IN STERILE PACKAGES

[75] Inventor: David H. Short, Coon Rapids, Minn.

[73] Assignee: Medtronic, Inc., Minneapolis, Minn.

[21] Appl. No.: 230,695

[22] Filed: Feb. 2, 1981

[51] Int. Cl.$^{3}$ .................... B65D 85/00; B65D 81/24; A61B 1/22

[52] U.S. Cl. .................................... 206/210; 206/364

[58] Field of Search ............... 206/210, 205, 362, 363, 206/364, 438, 204

[56] References Cited

U.S. PATENT DOCUMENTS

| | | | |
|---|---|---|---|
| 3,485,352 | 12/1969 | Pilger | 206/365 |
| 3,815,611 | 6/1974 | Denniston | 128/419 D |
| 3,967,728 | 7/1976 | Gordon et al. | 206/364 |
| 3,994,302 | 11/1976 | Brennen | 128/404 |
| 4,011,947 | 3/1977 | Sawyer | 206/363 |
| 4,141,366 | 2/1979 | Cross, Jr. et al. | 128/418 |

FOREIGN PATENT DOCUMENTS 2842318 9/1978 Fed. Rep. of Germany .

OTHER PUBLICATIONS

*New Pacemaker Electrodes, American Society Artifical Internal Organs,* vol. 29, pp. 29–35, 1971.

*Primary Examiner*—William T. Dixson, Jr.
*Attorney, Agent, or Firm*—Schroeder, Siegfried, Vidas, Steffey & Arrett

[57] ABSTRACT

Rehydration of hydrogel components in sterile packages.

13 Claims, 5 Drawing Figures

IN SITU REHYDRATING IN STERILE PACKAGES

DESCRIPTION

BACKGROUND OF PRIOR ART

It is desirable to rehydrate dry components such as dry hydrogel components in a specialized environment following packaging. Such a practice is desirable in the medical device industry, for example. One approach to environment maintenance has been to store such components within a package which includes a container that maintains the specialized internal environment. This environment is often a sterile condition. It is desirable that the hydrogel component be rehydrated in the package without compromising the sterile condition.

A specific example of a medical device having a hydrogel component of the type described above is a body implantable lead with hydrogel electrode, one type of which is a major component of the well-known cardiac pacemaker. Following manufacture, and prior to implantation, such leads are typically packaged in a container adapted to maintain a sterile internal condition during storage, shipment and intermediate handling. Unfortunately, during packaging and sterilizing, the hydrogel becomes somewhat dehydrated or dried. It must be rehydrated, usually about 24 hours prior to its use, without compromising its sterile condition. To accomplish this without compromising the sterility of the packaged lead is, at best, difficult.

BRIEF SUMMARY OF THE INVENTION

The present invention provides a package for a medical device having a hydrogel component, the package being of the type in which a container houses the device in such a manner that the hydrogel component can be rehydrated in situ while maintaining a specialized internal environment until opened. Rehydration may be completed on the container housed device without compromising the container internal environment. In a preferred embodiment, the package is adapted to contain a body implantable lead having a hydrogel electrode and to maintain a sterile internal condition, while closed, while allowing for the rehydration of the hydrogel in the container without compromising the internal container sterility.

The container may be formed in whole or in part by molding a gas permeable material such as polypropylene, through which sterilization is effected, to any desired container configuration. The container is provided with an externally accessible self-sealing inlet through which a quantity of rehydration fluid may be supplied to the interior of the container. Preferably, the hydrogel component is positioned in an inner receptacle in the container to which the rehydrating fluid is supplied. Preferably, the self-sealing inlet means comprises a self-sealing septum of the type which is penetrated for supplying the rehydrating fluid to the hydrogel component.

One prior art example of a medical device having a self-sealing septum is disclosed in U.S. Pat. No. 3,951,147 issued Apr. 20, 1976 to Tucker et al for IMPLANTABLE INFUSATE PUMP. The Tucker pump is a mechanical device which discharges and conducts fluid to an infusion site in the body. The unit is provided with an externally accessible inlet which, on implant, is situated close to the skin so that the pump can be refilled percutaneously. The Tucker inlet is closed by a self-sealing septum which is penetrated on refilling of the pump, penetration of the septum providing access to a reservoir within the implant which contains the infusate to be discharged. The Tucker patent is hereby incorporated by reference.

Self-sealing materials of the type employed by Tucker as a septum have been used in other implantable devices. For example, in many body implantable stimulators, an electrical and mechanical interconnection between the pulse generator and a stimulation energy delivering lead is established by a setscrew, the head of the setscrew being protected by a hood of a self-sealing material with the setscrew being engaged through the hood by a tool to establish the connection. On removal of the tool from the hood, the self-sealing material isolates the setscrew from body fluids.

DETAILED DESCRIPTION OF THE INVENTION

Figure 1:
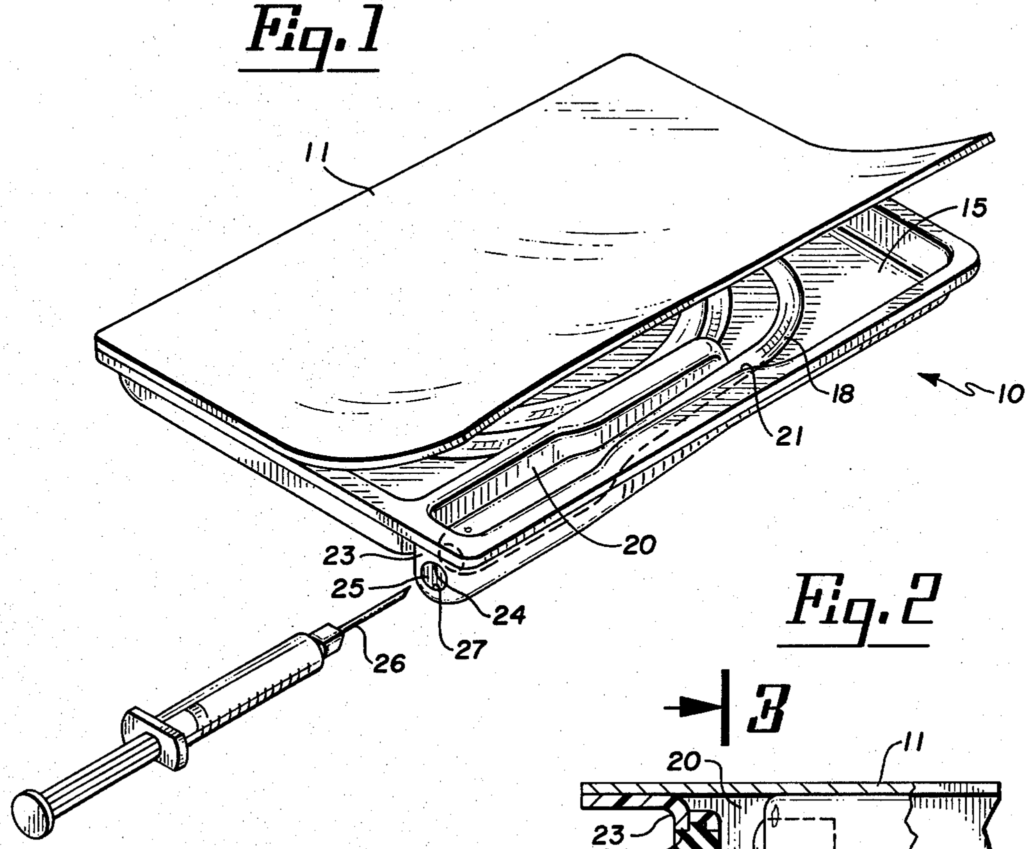
FIG. 1 is a perspective view of a component package by which the improvement of the present invention will be partially explained.
Figure 2:
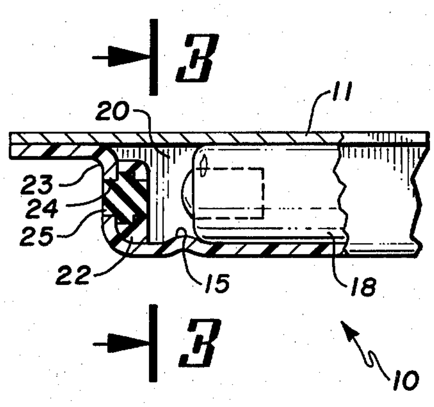
FIG. 2 is a cross-section taken along the line 2—2 in FIG. 1.

FIGS. 1 and 2 are illustrative of a preferred component package to which the improvement of the present invention may be applied. The package of FIG. 1 may be adapted to house one or more components and associated tools, leads, etc. Similarly, multiple components may be housed therein, dependent on the requirements at the ultimate location of component use. The package of FIGS. 1 and 2 is of a type known to the prior art which will maintain a specialized internal environment. Within the context of a body implantable component, that environment will typically be a sterile condition. Specifically, when the component is a body implantable lead with a hydrogel electrode, the package may contain the same and associated components as well as tools to facilitate their implantation. In outward appearance, the package of FIGS. 1 and 2 is formed of a container including a tray member generally designated at 10 and a gas permeable closure member 11. Closure member 11 allows sterilization of a housed electrical component, in known manner, while bearing indicia to identify the component, its manufacturer, its operating parameters, etc. Typically, sterilization of components housed within a package of the type illustrated is effected by placing the closed container within a pressurized atmosphere of ethylene oxide.

The elements described to this point in FIGS. 1 and 2 are known to the prior art and have been employed to contain components within the space 15 in a specialized atmosphere, a sterile condition for example, during storage, shipping and intermediate handling. An implantable lead 18 is illustrated coiled within space 15 in FIGS. 1 and 2. Lead 18 includes a hydrogel electrode component (not shown) which becomes dehydrated or partially dehydrated as a consequence of the sterilization process.

Ordinarily, access to lead 18 within space 15 to rehydrate the hydrogel component would require an opening of the closure member 11 thereby violating the specialized environment within space 15. It is desirable to have the facility to rehydrate the hydrogel component without violating the sterile condition within which it is housed. The present invention provides this facility.

Still with reference to FIGS. 1 and 2, tray 10 is illustrated with an inner receptacle 20 molded into a corner thereof against the intersecting walls of the container. Inner receptacle 20 has an open end 21 into which the hydrogel electrode (not shown) at one end of lead 18 may be positioned when it is packaged. A normally closed inlet means 22 is shown in the end wall 23 of the container and in communication with the interior of receptacle 20.

Figure 3:
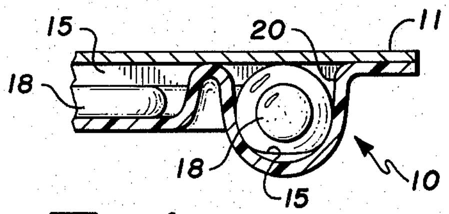
FIG. 3 is a fragmentary cross-section of the end wall of the package shown in FIGS. 1 and 2, taken along line 3—3 of FIG. 2.

In the preferred embodiment shown, referring particularly to FIG. 3, normally closed inlet means comprises an opening 24 in end wall 23 and a self-sealing septum 25 which may be molded into the opening in the wall. As already described hereinabove, self-sealing septums and the materials therefor are known.

For rehydration of the package contents, a syringe may be injected through septum 25 as by a needle 26, preferably having a blunt tip 27, is carried by a syringe (See FIG. 1). The blunt tip 27 will penetrate the self-sealing septum 25. As is known in the art, the use of a blunt tip enhances the ability of the self-sealing septum 17 to self-seal. By this means a quantity of fluid may be supplied to inner receptacle 20. This will be facilitated by standing the package on end i.e., on end wall 23. An inlet is thus provided through which a rehydrating fluid such as water may be supplied to receptacle 20 and hence to the hydrogel component on the lead without compromising the sterile content.

Obviously, many modifications and variations of the present invention are possible in light of the above teachings. For example, FIG. 4 illustrates an alternative which may be used.

Figure 4:
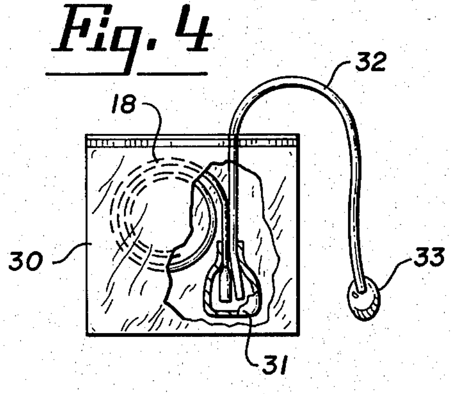
FIG. 4 illustrates an alternate embodiment to that illustrated in FIGS. 1 and 2.

With specific reference to FIG. 4, medical devices may also be packaged and sterilized in plastic bags such as polypropylene bags. As shown in FIG. 4, the invention may utilize such a bag 30 into which an implantable lead 18 is placed with the hydrogel tip thereof positioned in a container 31 which is also carried inside of bag 30. Container 31 may be of any type; a common test tube may be satisfactorily used. Also inserted into container 31 and extending exteriorally of bag 30 is a tube 32, such as a plastic capillary tube or the like, which is sealed at its outer end by a body of silicone rubber 33. Bag 30 is sealed, as by heat for example and subjected to known sterilization procedures. For example, the ethylene oxide procedure under pressure may be used. When it is desired to rehydrate the hydrogel tip of lead 18, the needle of a syringe may be inserted into tube 32 through the silicone rubber body 33 and rehydrating fluid is thereby supplied to container 31. Since the silicone rubber body 33 is self-sealing, removal of the syringe is accomplished without compromising the inner sterility of bag 30.

Figure 5:
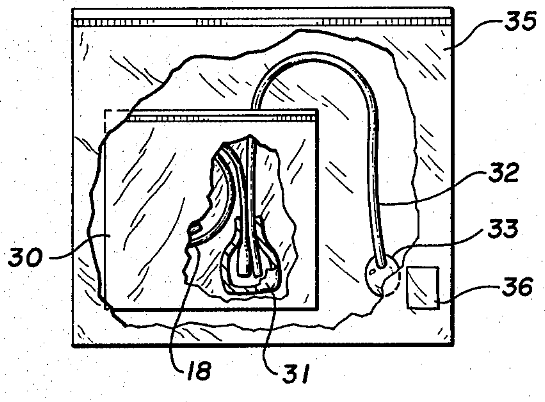
FIG. 5 illustrates an alternative to another portion of the embodiment illustrated in FIG. 4.

In some instances, it is desirable to "double bag". Such an arrangement is shown in FIG. 5 which includes the sealed bag 30 and its contents in a second, similar bag 35 which is in turn sealed but with the outer end of tube 32 inside of second bag 35. An amount of silicone rubber 36 is deposited on a selected site of the outside surface of bag 35 as shown. In some instances it may be desirable to roughen the surface of the bag at the attachment site in order to facilitate the adherence of the silicone rubber to the bag. When it is desired to rehydrate the hydrogel tip, tube 32 may be manipulated into the vicinity of the silicone rubber 36 and the syringe may be inserted through the rubber and the bag and into the tube as already described.

It is therefore to be understood that, within the scope of the appended claims, the invention may be practiced otherwise than as specifically described.

I claim:

1. In a package of the type having a container for housing an article including at least one dry component, the container being adapted to maintain a specialized internal environment until opened, the improvement comprising an inner receptacle housed within the container for receiving and holding the dry component, and normally closed inlet means communicating with the inner receptacle for introducing a quantity of hydrating fluid thereto to hydrate the dry component without compromising the container internal environment.

2. The package of claim 1 wherein the inlet means comprises septum means penetrable by a syringe needle and being self-sealing following penetration and withdrawal of such needle.

3. In a package of the type having a container for housing at least one dry component, the container being adapted to maintain a sterile internal condition while closed, the improvement which comprises means for allowing the introduction of hydrating fluid into the container without compromising internal container sterility.

4. The package of claim 3 wherein the means for allowing the introduction of fluid into the container comprises septum means penetrable by a syringe needle and being self-sealing following penetration and withdrawal of such needle.

5. The package of claim 1 or 3 wherein at least a portion thereof is comprised of a material capable of being permeable to a gaseous sterilant.

6. The package of claim 5 wherein the permeable material is polypropylene.

7. The package of claim 5 wherein the gaseous sterilant is ethylene oxide.

8. The package of claim 1 wherein the article is an implantable lead and the dry component is a hydrogel electrode carried thereby.

9. The package of claim 1 wherein the package container is a molded body, the inner receptacle is integrally molded on an inner wall thereof, and the inlet means is positioned in the wall so as to open into and communicate directly with the inner receptacle.

10. A package of the type having a container adapted to maintain a sterile internal condition; an implantable lead including a dry hydrogel electrode enclosed in the container; inner receptacle means in the container, the receptacle means receiving the hydrogel electrode and being adapted to hold a quantity of hydrating fluid, and inlet means communicating with the receptacle means for the introduction of hydrating fluid thereto without compromising internal container sterility.

11. The package of claim 10 wherein the inlet means comprises septum means penetrable by a syringe needle and being self-sealing following penetration and withdrawal of such needle.

12. The package of claim 11 wherein the package container is a molded body, the inner receptacle is integrally molded on an inner wall thereof, and the inlet means is positioned in the wall so as to open into and communicate directly with the inner receptacle.

13. The package of claim 12 wherein the inlet means comprises septum means penetrable by a syringe needle and being self-sealing following penetration and withdrawal of such needle.

* * * * *